United States Patent [19]

Chiccarelli

[11] 4,247,466
[45] Jan. 27, 1981

[54] LACTONE METABOLITES OF 3-(4-BIPHENYLYLCARBONYL)PROPIONIC ACID

[75] Inventor: Fortunato S. Chiccarelli, New City, N.Y.

[73] Assignee: American Cyanamid Company, Stamford, Conn.

[21] Appl. No.: 54,748

[22] Filed: Jul. 5, 1979

[51] Int. Cl.³ .................................... C07D 307/32
[52] U.S. Cl. .............................. 260/343.6; 424/279
[58] Field of Search .................................... 260/343.6

[56] References Cited

U.S. PATENT DOCUMENTS

| | | | |
|---|---|---|---|
| 3,784,701 | 1/1974 | Tomcufcik et al. | 424/317 |
| 3,859,256 | 1/1975 | Teufel et al. | 260/343.6 |
| 3,966,960 | 6/1976 | Ellenbogen et al. | 424/317 |
| 3,966,978 | 6/1976 | Ellenbogen et al. | 424/317 |
| 3,969,402 | 7/1976 | Adams et al. | 424/317 |
| 4,021,479 | 5/1977 | Seeger et al. | 260/343.6 |

OTHER PUBLICATIONS

Genge et al., Chem. Abst., vol. 52, 9039 g.

Primary Examiner—Henry R. Jiles
Assistant Examiner—Jane T. Fan
Attorney, Agent, or Firm—Norton S. Johnson

[57] ABSTRACT

Compounds of lactone metabolites of 3-(4-Biphenylylcarbonyl)propionic acid useful as anti-inflammatory and anti-platelet aggregation agents.

5 Claims, No Drawings

LACTONE METABOLITES OF 3-(4-BIPHENYLYLCARBONYL)PROPIONIC ACID

BACKGROUND OF THE INVENTION

This invention is concerned with the preparation and use of antithrombotic and anti-inflammatory drugs. Some of the prior examples of related compounds will now be considered. U.S. Pat. No. 3,966,978 to Ellenbogen et al. discloses the use of 4-biphenylacetic acid in the amelioration of blood platelet aggregation. U.S. Pat. No. 3,784,701 to Tomcufcik et al. discloses a group of anti-inflammatory drugs, substituted benzoylpropionic acids, including a biphenyl which is a starting material of some of the compounds of the invention.

U.S. Pat. No. 3,966,960 to Ellenbogen et al. is to the use of 3-(4-biphenylcarbonyl)propionic acid as an inhibitor of platelet aggregation. U.S. Pat. No. 3,784,704 to Cohen et al. describes the use and preparation of 4-biphenyl acetic acid in the amelioration of pain.

U.S. Pat. No. 3,969,402 to Adams et al. discloses the preparation and use of 2-(hydroxy substituted-4-biphenylyl)propionic acids as anti-inflammatory agents.

British Pat. No. 1,390,091 describes the preparation and use of 5-(4-biphenylyl)-2-hydro-2-(3H)-furanone. The activity of this compound is indicated as "antiphlogistic" and inhibitory toward "the aggregation of thromocytes".

Finally, an article by H. Yoshizawa, Y. Tada, T. Naruke and M. Mizumura; Basic Pharmacology and Therapeutics, 2, No. 11, Dec. 15, 1974, pp. 31-40 describes 3-(4-biphenylylcarbonyl)propionic acid and derivatives.

SUMMARY OF THE INVENTION

This invention is concerned with new compounds of the formula:

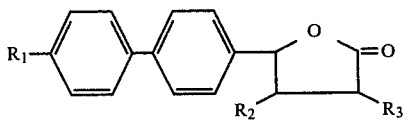

wherein $R_1$, $R_2$ and $R_3$ are each selected from the group comprising hydrogen and hydroxy and where $R_2$ and $R_3$ include both the cis and trans configurations.

This invention is also concerned with methods of treating inflammation and platelet aggregation, by the administration of compounds of the formula:

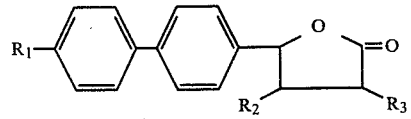

wherein $R_1$, $R_2$ and $R_3$ are as described above.

Specifically, these compounds include the following:
5-(4-Biphenylyl)dihydro-2-(3H)-furanone, a compound disclosed in British Pat. No. 1,390,091;
Dihydro-5-(4'-Hydroxy-4-biphenylyl)-2(3H)-furanone;
5-(4-Biphenylyl)dihydro-4-hydroxy-cis-2(3H)-furanone;
5-(4-Biphenylyl)dihydro-4-hydroxy-trans-2(3H)-furanone;
5-(4-Biphenylyl)dihydro-3-hydroxy-cis-2(3H)-furanone;
5-(4-Biphenylyl)dihydro-3α-hydroxy-trans-2(3H)-furanone.

DESCRIPTION OF THE INVENTION

The compound 5-(4-biphenylyl)dihydro-2-(3H)-furanone may be prepared by treating 3-(4-biphenylylcarbonyl)-propionic acid in basic medium with sodium borohydride. The addition of acetic acid precipitates a solid which is again treated with sodium borohydride in basic medium, and precipitated with glacial acetic acid giving 4-(4-biphenylyl)-4-hydroxybutyric acid. This product is treated with a mineral acid and then neutralized with sodium acetate giving the desired product.

The compound Dihydro-5-(4'-hydroxy-4-biphenylyl)-2(3H)-furanone may be prepared by treating 4'-methoxy-γ-oxo-4-biphenylbutyric acid with hydrogen bromide in acid to produce 4'-hydroxy-γ-oxo-4-biphenylbutyric acid. This in turn is treated with sodium borohydride as described above and then purified with organic solvents to produce the desired product.

The other compounds of this invention may be prepared as metabolites of 3-(4-biphenylylcarbonyl)propionic acid in warm-blooded animals.

For therapeutic administration, the compounds of this invention may be incorporated with excipients and used, for example, in the form of tablets, dragees, capsules, liquids, elixirs, emulsions, suspensions, syrups, chocolate candy, wafers, chewing gum and the like. Such compositions and preparations should contain at least 0.1% of active ingredient. The percentage in the compositions and preparations may, of course, be varied, and may conveniently be between about 2% and 60% or more of the weight of the unit. The amount of active component in such therapeutically useful compositions or preparations is such that a suitable dosage will be obtained. This dosage can also be obtained by the use of sustained release preparations. Preferred compositions or preparations according to the present invention are prepared so that a dosage unit form contains between about one and 250 mg. of active component.

Tablets, pills, dragees and the like may contain the following: a binder such as gum tragacanth, acacia, corn starch or gelatin; a disintegrating agent such as corn starch, potato starch, alginic acid or the like; a lubricant such as stearic acid, magnesium stearate, talc or the like; a sweetening agent such as sucaryl or saccharin may be added, as well as a flavoring such as peppermint, oil of wintergreen or cherry flavoring.

The compounds of the present invention are active as inhibitors of platelet aggregation.

The compounds were tested essentially according to the method of G. V. R. Born, Nature, No. 4832, pp. 927-929 (1962) and J. R. O'Brien, J. Clin. Path., 15, 446-452 (1962). Various concentrations of the test compounds were added in vitro to human platelet rich plasma. Collagen was added at a final concentration of 500 mcg./ml. to induce platelet aggregation. Inhibition of platelet aggregation was determined by direct comparison of the optical density of the plasma treated with the test compound and a control. The result of such a test on a representative compound of this invention appears in Table I.

TABLE I

| Compound | Concentration mcg/ml | Result |
|---|---|---|
| Dihydro 5-(4'-hydroxy-4-bi- | | |

TABLE I-continued

| Compound | Concentration mcg/ml | Result |
|---|---|---|
| phenylyl)-2(3H)-furanone | 0.25 | Accept |

The compounds of the present invention are active as anti-inflammatory agents.

The compounds were tested to determine their effect on conditions which result in inflammation by measuring the effect on ultraviolet induced erythema in guinea pigs. Albino guinea pigs were depilitated on their flanks, the evening before testing, with a standard mixture of barium sulfite and gum acacia. On the morning of the test, groups of 4 guinea pigs were dosed by gavage one hour (−1 hour) to ultraviolet exposure. At zero hour they were restrained in a plastic container which allows exposure of three circular spots. They were then exposed to ultraviolet irradiation from a "Hanovia" Kromayer lamp, model 10, for 60 seconds. At one and four hours the degree of erythema for each of the three sites was assessed according to the following scoring system.

0 = no erythema
0.5 = incomplete circle or faint erythema
1.0 = complete circle of distinct erythema Thus, the maximum score for each animal is 3.0. The results of this test on a typical compound of the present invention appears in Table II.

TABLE II

| Compound | Dose mg/kg | No. of Animals | Score (avg.) 1 Hour | Score (avg.) 4 Hours |
|---|---|---|---|---|
| 5-(4-biphenylyl)dihydro-2-(3H)-furanone | 250 | 8 | 0 | 2.1 |

DETAILED DESCRIPTION OF THE INVENTION

The particular embodiments of this invention are detailed in the following examples.

EXAMPLE 1

5-(4-Biphenylyl)dihydro-2(3H)-furanone

A 10.3 g. portion of 3-(4-biphenylylcarbonyl)propionic acid in 8 ml. of 6 N NaOH is treated with 15 g. of sodium borohydride and stirred for 2 hours. The cloudy solution is treated carefully over a 30 minute period with 25 ml. of glacial acetic acid producing a colorless precipitate. The solid is collected by filtration, washed with water and dried. A mixture of a 9 g. portion of this solid, 7.5 ml. of 6 N NaOH and 15 g. of sodium borohydride in 2 liters of water is stirred for 2 hours. The mixture is filtered and the filtrate is treated with glacial acetic acid giving 5 g. of 4-(4-biphenylyl)-4-hydroxybutyric acid.

A mixture of one g. of the above product, 75 ml. of warm (60° C.) glacial acetic acid and 0.25 ml. of $H_2SO_4$ is stirred for 30 minutes and then neutralized with an excess of sodium acetate. An equal volume of water is added causing the precipitation of a solid which is collected giving 5-(4-biphenylyl)dihydro-2(3H)-furanone.

EXAMPLE 2

Dihydro-5-(4'-Hydroxy-4-biphenylyl)-2(3H)-furanone

A 3.4 g. portion of 4'-methoxy-γ-oxo-4-biphenylbutyric acid (U.S. Pat. No. 2,590,085), 25 ml. of glacial acetic acid and 7.5 ml. of hydrogen bromide are refluxed for 18 hours. The mixture is cooled in ice and then filtered, giving 2.9 g. of 4'-hydroxy-γ-oxo-biphenylbutyric acid.

A 2.0 g. portion of the above product is added to 320 ml. of water. A 10 ml. portion of 1 N NaOH is added. A 3 g. portion of sodium borohydride is added and the mixture is stirred at room temperature overnight. The mixture is cooled in ice and 12 ml. of glacial acetic acid is added. The gelatinous precipitate is filtered through diatomaceous earth and washed with ether. The ether is evaporated giving a solid which is treated with water and filtered, giving a solid. The solid is triturated with benzene and the solid is recovered. This solid is dissolved in a small amount of ethyl acetate, benzene is added and the mixture is stored overnight in a chill room. The solid is recovered by filtration and air dried. The mother liquor crop (0.45 g.) is refluxed overnight in 20 ml. of xylene giving a solid which is crystallized from ethanol treated with activated charcoal giving the final product, m.p. 176.5°–181° C.

EXAMPLE 3 cis-5-(4-Biphenylyl)dihydro-4-hydroxy-2(3H)-furanone
and
trans-5-(4-Biphenylyl)dihydro-4-hydroxy-2(3H)-furanone These two products are derived as metabolic products from dogs. Two adult beagles, one male (9.2 kg.) and one female (7.3 kg.) are used. The dogs are fed 300 g. of Rockland Dog Diet (Tekland Inc., Monmouth, Illinois) once a day and have free access to water. On the day of the test each dog receives a sigle oral dose (100 mg./kg.) of $^{14}C$-3-(4-biphenylylcarbonyl)propionic acid sodium salt as a clear aqueous solution. The dogs were maintained individually in metabolism cages. Urine samples are collected as 24 hour cumulative samples in containers surrounded by dry ice, and stored in a deep freeze.

CHROMATOGRAPHY

The column support is acid washed and methanol rinsed Celite ® No. 545. The column is 1.5×45 cm. The solvent system is heptane:ethyl acetate:methanol:water:acetic acid (300:200:80:20:1.5). A 20 g. portion of the Celite is mixed with 10 ml. of the lower phase of the solvent system. The column is packed with 0.5 g. increments of the wet column support after placing a glass wool plug in the bottom. The packed column is about 35 cm. long.

A 100 ml. sample of the cumulative 24 hour urine from the dogs is heated with 5 N hydrochloric acid for 30 minutes in a boiling water bath. After cooling, the solution is extracted with a mixture of chloroform:ether (8:3). The solvent extract is evaporated under nitrogen and the residue is mixed with 5.0 ml. of lower phase and 10 g. of Celite and charged on the column. The column is eluted with upper phase. Fractions of 7.0 ml are collected and radioactivity is measured in either a Beckman LS-250 Liquid Scintillation Spectrometer or a Nuclear-Chicago, Mark I Liquid Scintillation Spectrometer. The desired metabolites are located by thin-layer chromatography and identified by ultraviolet, mass spectrometer, nuclear magnetic resonance and infrared absorption patterns.

EXAMPLE 4 cis-5-(4-Biphenylyl)dihydro-3-hydroxy-2(3H)-furanone
and
trans-5-(4-Biphenylyl)dihydro-3-hydroxy-2(3H)-furanone These two products are derived as metabolic products from guinea pigs. Nineteen normal guinea pigs from the Lederle colony are used. Their weight range is 290–340 g. The guinea pigs are fasted overnight before dosing. Drinking water and food are available throughout the test period. The guinea pigs receive a single oral dose of 100 mg. of $^{14}$C-3-(4-biphenylylcarbonyl)propionic acid sodium salt per kg. of body weight, administered as a clear aqueous solution. The guinea pigs are maintained individually in metabolism cages. The urine samples are collected as 24 hour cumulative samples in containers surrounded by dry ice and then stored in a deep freeze.

The chromatography used is the same as described in Example 3. Radioactivity is measured as described in Example 3.

A 40 ml. combined sample of the cumulative 24 hour urine from the guinea pigs is heated with 20 ml. of 5N-hydrochloric acid for 45 minutes in a boiling water bath. The mixture is cooled and extracted three times with a mixture of chloroform:ether (8:3). The solvent is evaporated under nitrogen. The residue is mixed with 1.0 ml. of the lower phase of the solvent system and 2.0 g. of Celite. The column is eluted with upper phase. Fractions of 3.0 ml. are collected and measured for radioactivity. The desired metabolites are located by thin-layer chromatography and identified by mass spectrometer, nuclear magnetic resonance and infrared absorption patterns.

EXAMPLE 5

Preparation of Compressed Tablets

| Ingredient | mg./Tablet |
| --- | --- |
| Active compound | 0.5–250 |
| Dibasic calcium phosphate N.F. | qs |
| Starch U.S.P. | 20 |
| Modified starch | 5 |
| Magnesium stearate U.S.P. | 1–3 |

EXAMPLE 6

Preparation of Hard Shell Capsule

| Ingredient | mg./Capsule |
| --- | --- |
| Active compound | 0.5–250 |
| Lactose spray dried | qs |
| Magnesium stearate | 1–5 |

EXAMPLE 7

Preparation of Oral Suspension

| Ingredient | % W/V |
| --- | --- |
| Active compound | 0.05–5 |
| Polysorbate 80 U.S.P. | 0.1 |
| Flavoring Agent | qs |
| Methylparaben U.S.P. | 0.18 |
| Propylparaben U.S.P. | 0.02 |
| Liquid sugar | 75.0 |
| Purified Water       qs | 100.00 |

Other embodiments of this invention will be obvious to those skilled in the art without departing from the spirit of the invention. The foregoing examples are merely illustrative of the invention which is limited solely by the claims.

I claim:

1. The compound, 5-(4'-hydroxy-4-biphenylyl)dihydro-2(3H)-furanone.
2. The compound cis-5-(4-biphenylyl)dihydro-3-hydroxy-2(3H)-furanone.
3. The compound trans-5-(4-biphenylyl)dihydro-3-hydroxy-2(3H)-furanone.
4. The compound cis-5-(4'-biphenylyl)dihydro-4-hydroxy-2(3H)-furanone.
5. The compound trans-5-(4-biphenylyl)dihydro-4-hydroxy-2(3H)-furanone.

* * * * *